United States Patent [19]

Chappell et al.

[11] Patent Number: 4,504,846
[45] Date of Patent: Mar. 12, 1985

[54] MULTIWAVELENGTH OPTICAL-TO-ELECTRICAL LOGIC OPERATIONS

[75] Inventors: Terry I. Chappell, Amawalk; Jerry M. Woodall, Bedford Hills, both of N.Y.

[73] Assignee: International Business Machines Corporation, Armonk, N.Y.

[21] Appl. No.: 454,747

[22] Filed: Dec. 30, 1982

[51] Int. Cl.³ ............... H01L 29/88; H01L 27/12; H01L 27/14; H01L 31/00
[52] U.S. Cl. .................................. 357/12; 357/30; 357/4; 307/311; 307/445; 307/322
[58] Field of Search ............ 357/30, 12, 4; 307/311, 307/445, 322

[56] References Cited

U.S. PATENT DOCUMENTS

| | | | |
|---|---|---|---|
| 3,040,178 | 6/1962 | Lyman et al. | 307/311 |
| 3,402,300 | 2/1966 | Pearl | 307/311 |
| 4,127,862 | 11/1978 | Ilegems et al. | 357/30 |

OTHER PUBLICATIONS

Electronics, Sep. 8, 1981, pp. 42 & 44.
Electronics Letters, vol. 16, No. 22, Oct. 23rd, 1980, pp. 836 & 837, "Planar-Doped Barriers in GaAs by Molecular Beam Epitaxy", by Malik et al.
Copending Application Ser. No. 311,091 filed 10/13/81, Freeouf et al., Copending Application Filed Concurrently Herewith, Ser. No. 454,784, Chappell et al.

Primary Examiner—Martin H. Edlow
Assistant Examiner—Eric Fallick
Attorney, Agent, or Firm—Alvin J. Riddles

[57] ABSTRACT

Optical-to-electrical logic operations may be performed employing as each logic variable a different light wavelength and providing an optical-to-electrical semiconductor converter such that each particular wavelength responsive optical energy receiving region is an up-doped region bounded by a thin tunneling junction having a thickness of the order of the mean free path of a carrier in the tunneling region.

11 Claims, 2 Drawing Figures

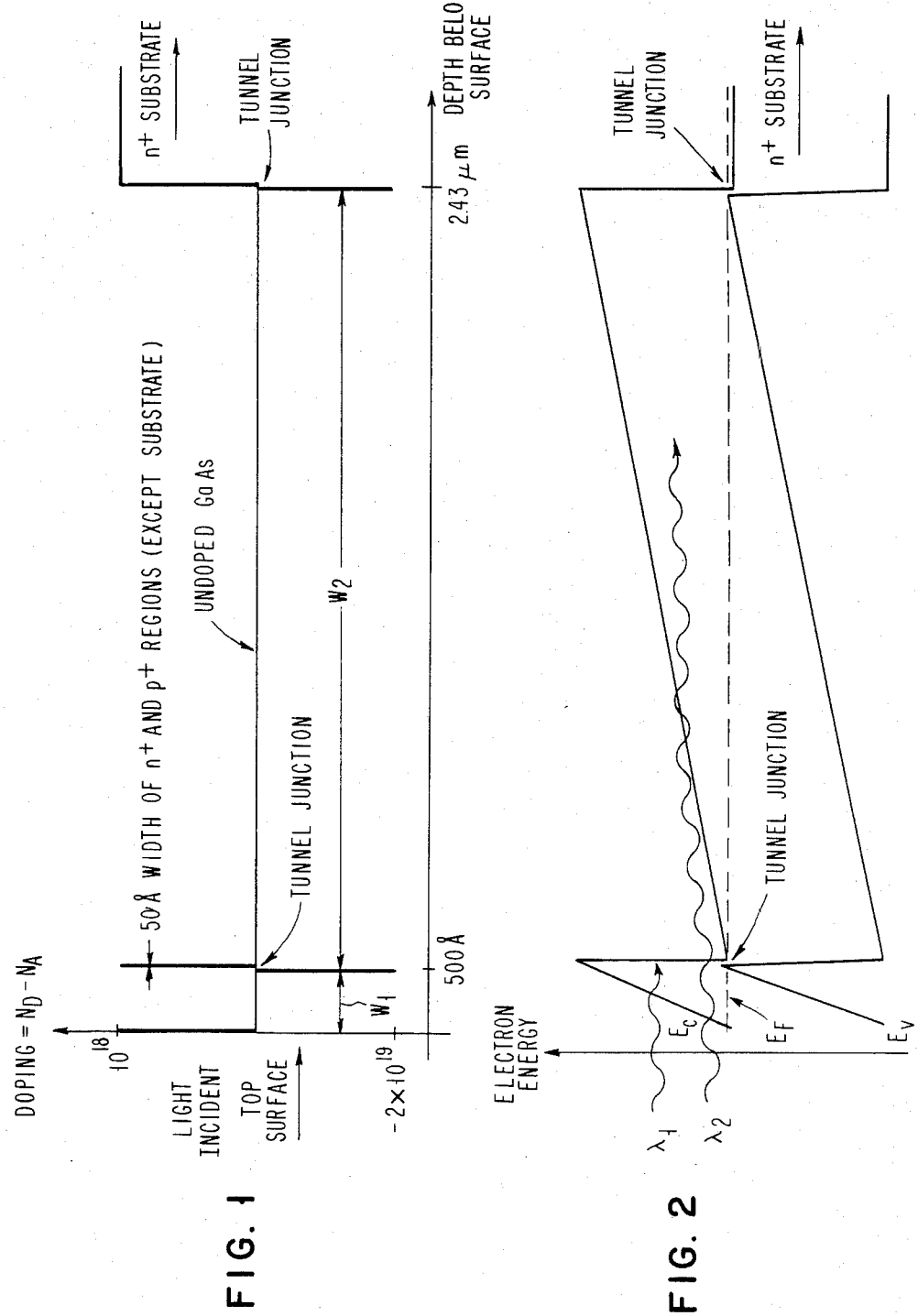

MULTIWAVELENGTH OPTICAL-TO-ELECTRICAL LOGIC OPERATIONS

DESCRIPTION

TECHNICAL FIELD

The technical field of the invention is in the combining of optical signals indicative of logic variables to produce a signal indicative of the logic combination. As speed and device densities increase, it is becoming more advantageous to transmit information signals in light beams and to route those light beams in conduits such as fiber optics. Logic signals that are in optical form are then logically combined in an element that produces an electrical signal. The logical combination operation, however, frequently introduces added structure and delays incompatible with speed capability requirements.

BACKGROUND ART

Logic signals in optical form have been combined in a single semiconductor structure wherein each logic variable is a different wavelength. The structure in which the logic combination takes place involves several semiconductor materials each having a different band gap for each different frequency. Such a structure is illustrated in Electronics, Sept. 8, 1981, page 42. In this complex heterostructure, diffusion is the carrier transport mechanism so that there will be a limit on speed of responsiveness.

In a copending application filed concurrently herewith, identified as Ser. No. 454,784, by the inventors Chappell, Jackson and Woodall, an optical conversion structural principle is set forth wherein in a semiconductor material with an undoped layer with a thickness of the order for ballistic transport bounded by a tunneling barrier that is of the order of the mean free path of a carrier in the tunneling portion of the semiconductor material, drift becomes the carrier transport mechanism and a much higher output voltage and higher speed of response is achieved.

BRIEF DESCRIPTION OF THE DRAWINGS

FIGS. 1 and 2 are a dimensionally correlated "AND" semiconductor structure doping profile and energy diagram, respectively, showing the physical conditions for the invention.

DISCLOSURE OF THE INVENTION

The invention is a semiconductor light-to-electrical signal converter for performing logic operations wherein light of a particular wavelength is used to represent a logic variable and a high speed of response output current or voltage represents the logic operator resulting from the logical combination of the logic variables involved.

In copending application Ser. No. 454,784 by inventors Chappell, Jackson and Woodall, filed concurrently herewith, an optical conversion structure is described wherein an undoped region bounded by a very thin tunneling p-n junction provides a simple high performance converter.

The converter of this invention provides in a semiconductor structure, serially positioned with respect to a light receiving surface, a structure similar to that of the copending application IBM Docket No. YO982-023, modified for logic conversion purposes by providing a separate undoped semiconductor region bounded by a thin tunneling junction of the order of the mean free path of a carrier in the tunneling region for each wavelength variable, each undoped region having a dimension so that maximum carriers are produced by the particular logic variable wavelength and of the order of less than 10% of the output current is produced by any other wavelength representing a logic variable.

The structure of the converter of the invention provides a high field as a result of the undoped regions being bounded by tunnel junctions. The high field in turn accelerates carriers produced by the specific logic variable light wavelength. The undoped condition of the region also minimizes carrier scattering as the light produced carriers move toward the boundary. The thickness dimension of the undoped region is long enough to provide maximum carriers produced by the light wavelength for that region.

These conditions permit drift rather than diffusion to be the dominant carrier transport mechanism so that logic signal results with only drift limited carrier transport delay are achieved. The tunneling boundaries provide low impedance to the drift transport of the carriers and are thin enough that no significant delay is introduced.

In order to facilitate explanation, the doping profile and materials composition have been set forth for a coincidence or "AND" logic function in the material GaAs which is chosen for its high optical-to-electrical conversion efficiency and mobility. It will, however, be clear to one skilled in the art in the light of the principles set forth that other semiconductor materials may be employed. Similarly, since all logic operators can be achieved by combinations of coincidence or "AND", presence or "OR" and denial or "NOT", and since NOT can be achieved by a presence signal interrupting an existing bias and since presence can be achieved by a single photodetector; the achieving of coincidence or "AND" being the most complex one skilled in the art can readily translate the principles set forth to logic involving combinations of "AND", "OR" and "NOT".

BEST MODE FOR CARRYING OUT THE INVENTION

Referring to FIGS. 1 and 2, a schematic of the doping profile with distance in an "AND" structure is shown dimensionally correlated with an energy level diagram.

The structure is a two logic variable-coincidence or "AND" structure. The structure has a separate undoped region for each logic variable arranged serially as planar regions under a light incident top surface above a substrate. The logic variables are introduced through the light incident surface in separate wavelength signals for each variable. The separate wavelength logic variable signals may be delivered independently or modulated in a single beam. In FIGS. 1 and 2, the logic variable signals enter from the light incident surface along the X or abscissa axis. In FIG. 1, the doping of the structure would be along the Y or ordinate axis. The degenerate doping of the tunneling boundaries occurs such a short distance that a line is shown. The logic variable conversion undoped region, adjacent the light incident surface would be tailored for the shorter wavelength and the region further below the light incident surface for the longer wavelength.

The logic variable conversion undoped regions are bounded by quantum mechanical tunneling junctions having a width dimension of the order of the mean free path of a carrier in the tunneling junction region. In most materials and particularly in GaAs, 50 Å is a sufficient distance. In FIG. 1, the boundary tunneling junctions are shown as 50 Å wide regions of n+ and p+ adjacent each other. The combined n+ and p+ distances of 100 Å are in toto of the order of the mean free path of a carrier in the tunneling region of the GaAs material.

The thickness dimension of each logic variable conversion region is tailored to absorb of the order of 90% of the light of the wavelength of the logical operator to which it is to be responsive.

The total depth from the light incident surface to the substrate is at least the depth of penetration of the light wavelength for the logic variable to be absorbed in the region next to the substrate. This is the longest wavelength logic variable signal.

The dimensions and the wavelengths are selected to discriminate between logical variables such that of the order of 90% of all the light of one wavelength is absorbed yet will not produce more than of the order of 10% of the current in the region for another wavelength. The 90% and 10% values are selected for good signal to noise ratios. In conditions where needed closer discrimination can be achieved with tighter structure and wavelength limitations.

Referring to FIGS. 1 and 2 together, the first active region is arranged to produce a large photocurrent response to light at wavelength $\lambda_1$ yet only have less than 10% of the photocurrent produced by light at wavelength $\lambda_2$ which passes through the region for $\lambda_1$. Similarly, the region further from the surface responds to light at wavelength $\lambda_2$. $\lambda_1$ is less than $\lambda_2$. Tailoring of the photocurrent response of the two active regions is done by varying either singly or together the thickness or band gap through material composition of each region. The greater the separation in wavelengths between the signals representing logic variables the less strenuous the discriminating ability between the regions need be. Where the logic variable requirements are such that the wavelengths become closer, both band gap and thickness differentiation become more essential.

The logical variable $\lambda$ selection and the conversion region parameters should be such that each separate region has a quantum efficiency for the desired wavelength that is such that the effects of other wavelengths do not exceed 10%. For the device embodiment of FIG. 1 using single undoped GaAs material, the quantum efficiency of the first logic variable conversion region having a thickness $W_1$ of 0.5 μm for a $\lambda_1$ of 0.425 μm is 90% and for a $\lambda_2$ of 0.78 μm the efficiency would be 6.9% in the same region. In the second logic variable conversion region having a thickness $W_2$ of 1.9 μm, the quantum efficiency would be 90% for $\lambda_2$ but would be 10% for $\lambda_1$ in that region.

For the material undoped GaAs where the doping level is less than $10^{16}$ atoms per cc, electric fields of 3500 V/cm may exist in each undoped region. The thickness of each region is selected so that high absorption and high photocurrent for the particular wavelength occurs. Since any other logic variable representing wavelengths would provide only 10% of the photocurrent, there would be output signal level photocurrent through the combined regions only when the wavelength signal for each region in combination is present.

In operation, under no bias voltage, the "AND" logic operator is developed between an ohmic contact to the substrate and a surface contact such as a grid or transparent ohmic contact. When the device of this invention is illuminated by two distinct monochromatic light wavelengths, which may be contained in a single beam, each representing a logical variable appreciable output signal level photocurrent can flow through the device. If only one of either of the wavelengths is present, very little photocurrent can flow since the regions are in series. Thus, the device of this invention acts as an optical AND gate, providing an appreciable current only when both light wavelengths are present. In extending the principle set forth it will be apparent that any number of logic variable conversion regions in series will result in an output logic operator current being the logical coincidence or "AND" function of all the input logic variable wavelengths.

In a structure employing the principles of the invention, since the photogenerated carriers are transported by drift rather than diffusion, a very fast transient response is achieved so that extra logic delay does not occur.

Referring again to FIGS. 1 and 2, the limiting transient response of the device is governed by the transit time of the widest undoped region shown by the dimension $W_2$. This is because the photocarriers are collected simultaneously by both the regions so that with essentially equal crystal conditions the widest region will be the slowest. For the device of FIG. 1, the transit time follows the relationship in Equation 1 using the values for GaAs and the dimensions of FIG. 1.

$$t_r = \frac{W_2}{v_s} = \frac{24 \times 10^{-5} \text{ cm}}{10^7 \text{ cm/sec}} = 24 \text{ picoseconds} \qquad \text{Eq. 1}$$

where
 $t_r$ is the transit time, and
 $v_s$ is the saturation drift velocity.

In the light of the principles of physics employed in the structure that have been set forth, it will be apparent that many substitutions will be available. For example, very thin regions could be achieved by growing epitaxially the two regions from two different semiconductor materials which are selected to have high absorption coefficients at two different wavelengths. In other words, substitute the undoped GaAs region material with the thickness $W_1$ with a material such as GaAlAs with a larger band gap and hence the other region if made of GaAs can have a smaller dimension $W_2$. This would permit more regions within the depth of penetration capability of certain frequencies.

The device of FIGS. 1 and 2 can be made by the technique of molecular beam epitaxy to grow the undoped regions as a single crystal. The tunneling barriers can be formed between regions of the crystal using the planar doping molecular beam epitaxial techniques such as described in Electronics Letters 16, 22, page 836, Oct. 23, 1980.

The p+ regions of the device are preferably more safely made using Mg as the dopant rather than Be which is standard in the art but which being poisonous is a source of handling difficulties. Efficient doping with Mg may be achieved using a volatile oxide suppression technique as described in copending application Ser. No. 311,091 filed Oct. 13, 1981.

What has been described is a semiconductor structure for optical-to-electrical logical operations wherein for each logic variable represented by a given wavelength an undoped individual layer of the structure bounded by a thin tunneling junction having a dimension of the order of the mean free path of a carrier in the tunneling region and the undoped region has a dimension tailored for maximum absorption of carriers.

Having thus described our invention, what we claim as new and desire to secure by Letters Patent is:

1. An optical-to-electrical logic element for providing a logic function signal in response to at least one logic variable signal comprising in combination at least one monocrystalline semiconductor essentially planar undoped region bounded by a quantum mechanical tunneling junction region having a thickness dimension of the order of the mean free path of a carrier in said tunneling junction region, said undoped region being essentially parallel to a light incident surface and having a thickness dimension correlated with maximum absorption of light of a particular wavelength, means delivering at least one light signal of a particular wavelength representing a specific logic variable, and sensing means for detecting across at least said region and said tunneling junction at least one of an electric current and voltage indicative of a logic function represented by said logic variable representing light means.

2. The element of claim 1 wherein said semiconductor is GaAs.

3. The element of claim 1 wherein said at least one semiconductor essentially planar undoped region includes in a single semiconductor material first and second regions, each having a different thickness dimension.

4. The element of claim 3 wherein each said first and second regions provide less than 10% photocurrent from light of the other region wavelength.

5. The element of claim 3 wherein said semiconductor material is GaAs, said thickness dimension of said first region is 0.5 micrometers, said thickness dimension of said second region is 1.9 micrometers, the light signal wavelength of a first logic variable is 0.425 micrometers and the light signal wavelength of a second logic variable is 0.78 micrometers.

6. In a logic element responsive to a combination of light signals representing logic variables employing a separate light wavelength responsive semiconductor region for each logic variable, the improvement comprising:

a separate light responsive undoped region bounded by a tunneling junction region wherein the thickness of said tunneling junction region is of the order of the mean free path of a carrier in said junction region, for each light logic variable signal, serially positioned with respect to a light incident surface, each said light responsive region having a thickness dimension to maximize absorption for light of the wavelength to which the region is to be responsive and to provide less than 10% of the photocurrent from any other wavelengths.

7. The element of claim 6 wherein said semiconductor is GaAs.

8. An optical-to-electrical logic element comprising in combination a semiconductor logic conversion element having at least one monocrystalline semiconductor material undoped region bounded by a tunneling p-n junction of the order of the mean free path of a carrier in said tunneling junction, positioned planar to a light incident surface within a light penetration distance of said light incident surface, logic signal detection means connected across said conversion element, and means directing light having a wavelength for each logic variable on said light incident surface.

9. The logic element of claim 8 wherein said conversion element is a unitary monocrystalline body having a plurality of undoped regions, each bounded by a tunneling p-n junction having a thickness of the order of the mean free path of a carrier in said junction region, and said undoped regions being arranged serially with depth of penetration of light through said light incident surface.

10. The logic of claim 9 wherein each said undoped region has a thickness dimension of an order to absorb of the order of 90% of light of a particular wavelength representing a logic variable for which it is to respond, and to absorb of the order of less than 10% of light of a wavelength assigned to another logic variable.

11. The logic element of claim 10 wherein said semiconductor material is GaAs, said plurality of undoped regions is two, the thickness dimension of the undoped region adjacent said light incident surface is 0.5 micrometers to respond to a logic variable wavelength of 0.425 micrometers and the thickness dimension of a second undoped region remote from said light incident surface is 1.9 micrometers to respond to a logic variable wavelength of 0.78 micrometers.

* * * * *